Sept. 5, 1950 E. S. BOERNER Plant Pat. 978
ROSE PLANT
Filed Sept. 19, 1949
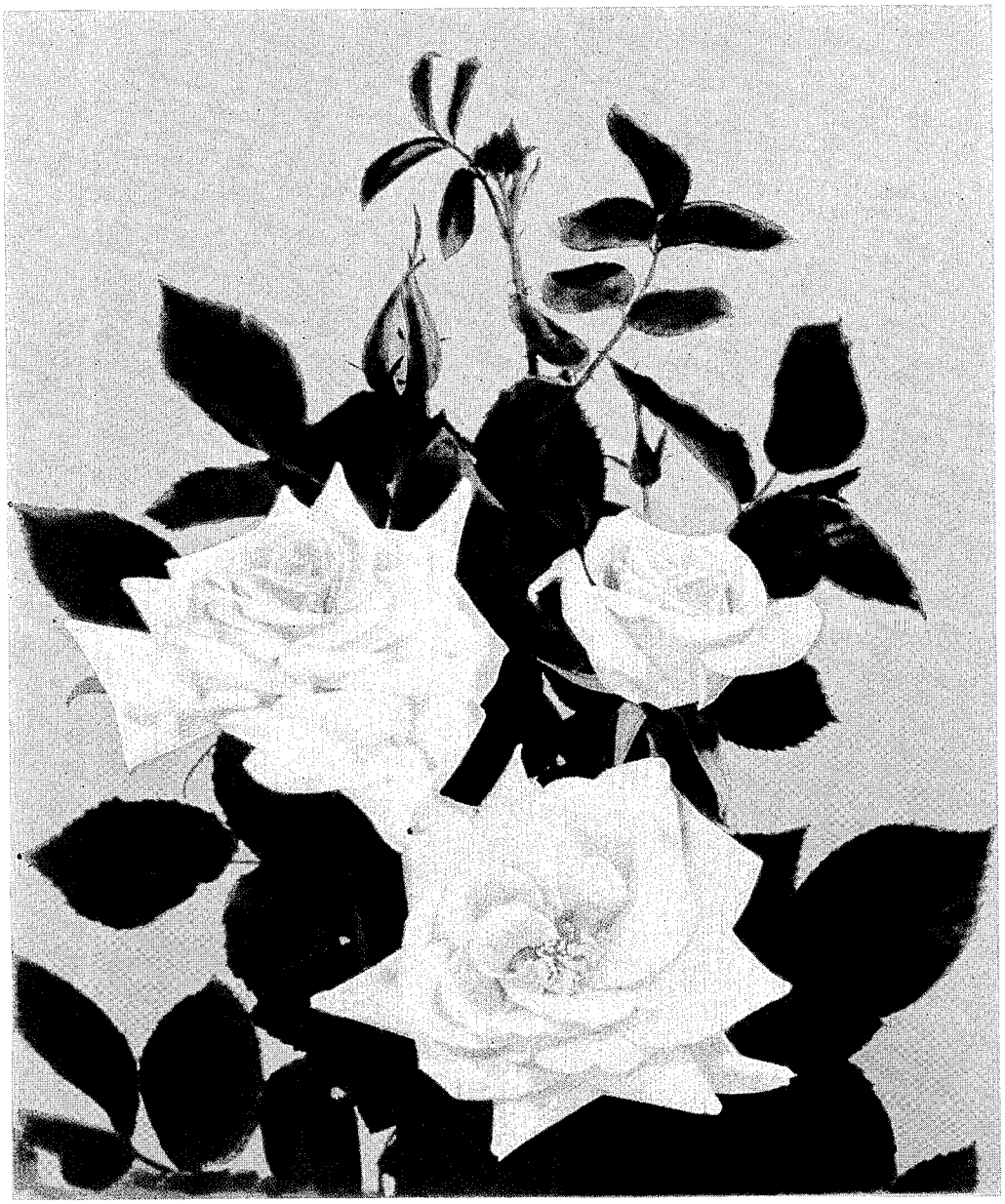
Inventor
E. S. Boerner
By Robb & Robb
Attorneys Patented Sept. 5, 1950

Plant Pat. 978

UNITED STATES PATENT OFFICE

978

ROSE PLANT

Eugene S. Boerner, Newark, N. Y., assignor to Jackson & Perkins Company, Newark, N. Y., a corporation of New York Application September 19, 1949, Serial No. 116,578

1 Claim. (Cl. 47—61)

The present invention relates to a new distinct variety of rose plant, resulting from a cross of a self-seedling of the variety "Eclipse" (Pl. Pat. #172) with similar characteristics and "R. M. S. Queen Mary" (Pl. Pat. #249).

This new variety is characterized as to novelty by its profuse production of hybrid tea flowers in their attractive color, shape and form; the profuse quantity of narrow thorns on the flowering stalk with prickles interspersed between them and the quick return of flowers after cutting, thereby enhancing the value of the variety as used for cut flower purposes.

In respect to the production characteristic, this new variety produces fifty percent more per plant than the "Briarcliff" varieties.

Asexual reproduction of this new variety shows the foregoing characteristics come true to form and are established.

The accompanying drawing illustrates the distinctive characteristics of the flowers at different stages of development from bud to full blown flowers.

This new variety was asexually reproduced at Newark, New York, by budding.

The following is a detailed description of the new variety, reference to color being in accordance with Ridgway's Color Standard and Nomenclature:

Parentage: Seedling.

*Seed parent.*—Self-seedling of "Eclipse."

*Pollen parent.*—"R. M. S. Queen Mary."

Classification: Botanic and commercial—hybrid tea.

*Flower*

(Observations made at Newark, New York, in greenhouse in the month of December in the afternoon.)

Blooming habit: Recurrent—continuous—very profusely recurrent.

Bud:

*Size.*—Medium.

*Form.*—Long; pointed. Is not affected by wet or hot weather.

*Color.*—When sepals first divide—Scarlet Red, Plate I. When petals begin to unfurl—Begonia Rose, Plate I. When half blown—inside of petals—Grenadine Pink, Plate II; reverse of petals—Orient Pink, Plate II.

*Sepals.*—Slightly serrated; branched. Curl back when petals begin to unfurl. Color—inside—Lumiere Green, Plate 17; outside—Lettuce Green, Plate 5.

*Calyx.*—Shape — funnel. Size — small. Aspect—smooth. Odor when rubbed—none. Color—Apple Green, Plate 17.

*Peduncle.* — Length — medium. Aspect—prickly. Color—Biscay Green, Plate 17. Strength—erect; slender.

*Opening.*—Opens up well. Is not affected by adverse weather conditions.

Bloom:

*Size.*—Medium. Average size when fully expanded, 4½ inches.

*Borne.*—Singly.

*Stems.*—Medium length; normal strength.

*Form.*—When first open—high center. Permanence—retains its form to the end; outer petals quill.

*Petalage.*—Double (full but open center). Number of petals under normal conditions, 45.

*Color.*—Center of flower—Grenadine Pink, Plate 2. Outer petals—Orange Pink, Plate 2, suffused with Capucine Buff, Plate 3. Base of petals (aiglet)—Strontian Yellow, Plate 16. Inside of petals—Pale Orange Yellow, Plate 3, overcase with Orient Pink, Plate 2. Reverse of petals—Orient Pink, Plate 2. General tonality from a distance—Pale Orange Yellow, Plate 3, overcast with Orient Pink, Plate 2.

*Discoloration.*—General tonality at end of first day—Pale Orange Yellow, Plate 3, overlaid with Orient Pink, Plate 2. Second day—Pale Orange Yellow, Plate 3. Third day—Shrimp Pink, Plate 1.

Petals:

*Texture.*—Leathery. Is not affected by wet or hot weather.

*Appearance.*—Inside — shiny; outside — satiny.

*Form.*—Oval; pointed

*Arrangement.*—Informal (with "rags" in center). Petaloids in center—few; large.

*Persistence.*—Drop off cleanly.

*Fragrance.*—Slight. Nature—tea (average hybrid tea scent).

*Lasting quality.*—On the plant and as cut flower—long.

Genital organs:

*Stamens, anthers.*—Medium size; few. Color—Apricot Yellow, Plate 4. Arrangement regular around styles.

*Stamens, filaments.*—Medium length. Color—Pinard Yellow, Plate 4.

*Pollen.*—Color—Buff Yellow, Plate 4.

*Styles.*—Bunched; uneven length; short; thin. Color—pistil, Pomegranate Purple, Plate 12.

*Stigmas.*—Color—Sulphur Yellow, Plate 5.

*Ovaries.*—Some protruding from calyx.

*Plant*

Form: Bush.

Growth: Vigorous; upright.

Foliage: 5 to 7 leaflets.

*Size.*—Large.

*Quantity.*—Abundant.

*Color.*—New foliage: upper side—Calla Green; Plate 5; serrations Oxblood Red, Plate 1; under side—Yellowish Oil Green, Plate 5; serrations Oxblood Red, Plate 1. Old foliage: upper side—Varley's Green, Plate 18; under side—Bice Green, Plate 17.

*Shape.*—Oval pointed.

*Texture.*—Upper side—leathery. Under side—smooth. Ribs and veins—ordinary.

*Edge.*—Serrated (saw toothed).

*Serration.*—Single; small.

*Leaf stem.*—Color—Light Bice Green, Plate 17. Under side—prickles.

*Stipules.*—Medium length; smooth.

*Disease resistance.*—Immune.

Wood:

*New wood.*—Color—Lettuce Green, Plate 5. Bark—smooth.

*Old wood.*—Color—Bice Green, Plate 17. Bark—smooth.

Thorns:

*Thorns.*—Quantity—on main stalks from base and on laterals from stalk—many. Form—narrow base; medium length; hooked downward. Color when young—Nopal Red, Plate 1. Position—irregular.

*Prickles.*—Quantity—on main stalks—few; on laterals—none. Color—Absinthe Green, Plate 31.

*Short needles.*—On main stalks and laterals—none.

I claim:

A new and distinct variety of hybrid tea rose plant, characterized as to novelty by its profuse production of flowers; the color, shape and form of said flowers; the profuse quantity of narrow thorns and interspersed prickles on the flowering stalks; and the quick return of flowers after cutting, substantially as shown and described.

EUGENE S. BOERNER.

No references cited.